(12) United States Patent
Franson et al.

(10) Patent No.: US 6,197,787 B1
(45) Date of Patent: *Mar. 6, 2001

(54) PHARMACEUTICAL FORMULATIONS CONTAINING POORLY SOLUBLE DRUG SUBSTANCES

(75) Inventors: Nancy M. Franson, Collegeville; Micael A. Guillot, Malvern; Sharon M. Laughlin, Phoenixville; William L. Rocco, Reading, all of PA (US)

(73) Assignee: Sanofi-Synthelabo, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/410,600

(22) Filed: Oct. 1, 1999

Related U.S. Application Data

(63) Continuation-in-part of application No. 09/028,504, filed on Feb. 24, 1998, now abandoned, which is a continuation-in-part of application No. 08/813,946, filed on Mar. 3, 1997, now Pat. No. 5,837,714, which is a continuation-in-part of application No. 08/808,761, filed on Mar. 3, 1997, now Pat. No. 5,760,056, which is a continuation-in-part of application No. 08/810,560, filed on Mar. 3, 1997, now Pat. No. 5,776,987.

(51) Int. Cl.[7] ............... A61K 31/70; A61K 31/4709; A61K 31/1902; A61K 31/08
(52) U.S. Cl. .................. 514/313; 514/23; 514/569; 514/723
(58) Field of Search .................. 514/313, 569, 514/23, 723

(56) References Cited

U.S. PATENT DOCUMENTS

| | | | |
|---|---|---|---|
| 5,071,643 | 12/1991 | Yu et al. | 514/570 |
| 5,096,926 | 3/1992 | Fiorini et al. | 514/569 |
| 5,342,625 | 8/1994 | Hauer et al. | 424/455 |
| 5,420,141 | 5/1995 | Biogegrain et al. | 514/314 |
| 5,633,009 | 5/1997 | Kenealy et al. | 424/448 |
| 5,681,606 | 10/1997 | Hutchison et al. | 426/590 |
| 5,760,056 | 6/1998 | Laughlin et al. | 514/314 |
| 5,776,987 | 7/1998 | Rocco et al. | 514/778 |
| 5,837,714 | 11/1998 | Rocco et al. | 514/313 |

FOREIGN PATENT DOCUMENTS

| | | |
|---|---|---|
| WO88/02625 | 4/1988 | (WO) . |
| WO95/00123 | 1/1995 | (WO) . |
| WO98/38987 | 9/1998 | (WO) . |

OTHER PUBLICATIONS

Sirenius et al., J. Pharm. Sci., 66, No. 6, Jun. 1979.

Sheen et al. Intl. Jrnl. Pharmaceutics, 118, (1995) 221–227.

March et al., Journal of the Assoc. Off. Anal. Chem., vol. 50, No. 2, pp. 457–462, 1967.

*Primary Examiner*—Phyllis G. Spivack
(74) *Attorney, Agent, or Firm*—Michael D. Alexander; Paul E. Dupont

(57) ABSTRACT

A method for preparing pharmaceutical formulations of poorly soluble drug substances in the form of concentrated solutions for filling soft gelatin capsules and solid dispersions and suspensions for filling hard gelatin capsules and compressing into tablets is provided. Pharmaceutical formulations of poorly soluble drug substances are also disclosed. The formulations include the sodium salt of the poorly soluble drug substance, a conversion aid such as PEG, polysorbate, a sugar alcohol (e.g. mannitol or xylitol), propylene glycol or transcutol, and, in some cases an excipient, such as dicalcium phosphate dihydrate, lactose monohydrate, or microcrystalline cellulose.

50 Claims, No Drawings

PHARMACEUTICAL FORMULATIONS CONTAINING POORLY SOLUBLE DRUG SUBSTANCES

CROSS-REFERENCE TO RELATED APPLICATIONS

This application is a continuation-in-part of copending application Ser. No. 09/028,504, filed Feb. 24, 1998, now abandoned, which was a continuation-in-part of applications Ser. No. 08/813,946, Ser. No 08/808,761 and Ser. No. 08/810,560, each of which was filed on Mar. 3, 1997, now U.S. Pat. No. 5,837,714, No. 5,760,056 and No. 5,776,987, respectively.

FIELD OF THE INVENTION

This invention relates to pharmaceutical formulations comprising a poorly soluble drug substance and a pharmaceutically acceptable carrier.

BACKGROUND OF THE INVENTION

Poorly soluble drug substances have been formulated in pharmaceutically acceptable carriers by finely dividing them, by grinding, into nanoparticles having an effective average particle size of less than 400 nm in order to achieve satisfactory bioavailabiity. However, to keep the nanoparticles from coagulation various surface active agents were used. Such agents may not be desirable and they also reduce the overall amount of the drug which otherwise could be contained in an effective dosage formulation.

Solid dispersions have also been used to increase the dissolution rate and bioavailability of drugs that are poorly water soluble. The carriers used have been physiologically inert compounds that are readily water soluble, such as polyethylene glycols. Two techniques which have been used to prepare solid dispersions are the fusion technique and the solvent technique. In the fusion technique, the drug substance is dissolved in a molten carrier and the mixture cooled to form a solid. In the solvent technique, drug substance and carrier are dissolved in a solvent, followed by removal of the solvent by evaporation or freeze drying.

The preparation of solid dispersions featuring good pharmaceutical properties is difficult. Problems which frequently occur during preparation include: degradation of drug substance at the temperature of the molten carrier; reaction of the drug with the molten carrier; and incomplete solidification of the product, e.g., the carrier remaining largely amorphous. Solid dispersions prepared from esters of p-aminobenzoic acid and xylitol are disclosed, for example, by Sirenius et al., *J. Pharm. Sci.,* 66, No. 6, Jun. 1979.

The present invention is directed to pharmaceutical formulations containing poorly soluble drug substances and particularly to SR 48692 which has shown considerable promise as an NT-antagonist for the treatment of psychosis. SR48692 and a method for the preparation thereof are described by Boigegrain et al in U.S. Pat. No. 5,420,141 (Example 13). SR48692 has the structural formula:

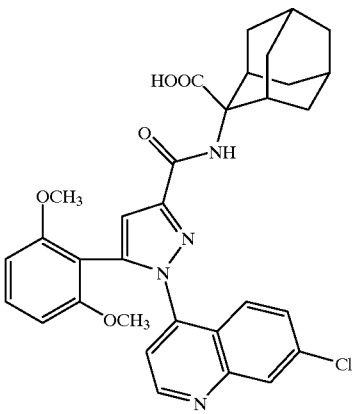

SR48692 has proven to be unusually difficult to formulate into pharmaceutical compositions, due in part to its very low solubility, even in organic solvents.

PCT/US87/02629 discloses a solvent system for enhancing the solubility of an acidic, basic or amphoteric pharmaceutical agent to produce a concentrated solution suitable for soft gelatin capsule filling. The solvent system comprises polyethylene glycol containing 0.2–1.0 mole equivalents of an ionizing agent per mole equivalent of pharmaceutical agent and 1–20% water. Attempts to formulate SR48692 in such a solvent system were not successful.

Sheen et al. in *Int. J. Pharm.,* 118(2), 221–7, 1995, disclose a solid dispersion of a poorly water-soluble drug, RP69698 prepared by a melting method with water-soluble carriers in which RP69698 is highly soluble. When incorporated into a solid dispersion, the formulation contains PEG 3350, Transcutol and Labrasol.

SUMMARY OF THE INVENTION

We have now discovered that poorly soluble drug substances may be incorporated into pharmaceutically acceptable carriers containing certain solvents and employing processes disclosed herein.

The invention can be practiced with a wide variety of drug substances. The drug substance preferably is present in an essentially pure form. The drug substance may be poorly soluble and must be soluble in at least one liquid medium. By "poorly soluble" it is meant that the drug substance has a solubility in an aqueous medium of less than about 10 mg/ml, and preferably of less than about 1 mg/ml.

Suitable drug substance can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-phannaceuticals, sex hormones (including steroids), anti-allergic agents, stimulants and anoretics, sympathomimetics, thyroid agents, vasodilators and xanthines. Preferred drug substances include those intended for oral administration. A description of these classes of drugs and a listing of species within each class can be found in Martindale, the extra Pharmacopoeia, Twenty-ninth Edition, the Pharmaceutical Press, London, 1989, the disclosure of which is hereby incorporated by reference in its entirety. The drug substances are commercially available and/or can be prepared by techniques known in the art.

Preferred drug substances for the purposes of the present invention include Naproxyn and compound SR48692.

Naproxyn is (S)-6-methoxy-(α-methyl-2-naphthaleneacetic acid, having the chemical structure

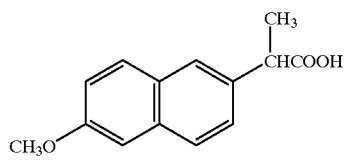

is well known in the prior art, and its preparation is disclosed, for example, in U.S. Pat. Nos. 3,904,682 and 4,009,197.

SR48692 is disclosed in U.S. Pat. No. 5,420,141 in Example 13, having the chemical structure

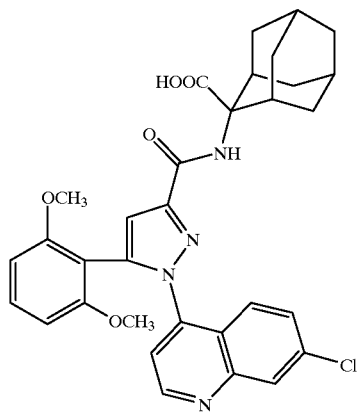

said patent is incorporated herein by reference.

Solid Dispersions IA and IB

IA) We have discovered, as disclosed in prior application Ser. No. 08/813,946, that the combination of Transcutol (diethyleneglycol monoethyl ether) and xylitol provides a carrier for solid pharmaceutical dispersions which can reduce impurities and/or degradation products. The dispersion maintains a high degree of crystallinity, exhibits acceptable hygroscopicity, rapidly dissolves in water and has good bioavailability.

In accordance with the invention, there is provided a solid dispersion comprising a poorly soluble drug substance, Transcutol and xylitol.

In another embodiment of the invention, there is provided a method of preparing such dispersion comprising the steps of dissolving a poorly soluble drug substance in Transcutol and adding the solution to xylitol.

IB) During further research we have discovered that Transcutol can be replaced with propylene glycol using a spray granulation process within a fluid bed. The process comprises the steps of:

a) preparing a drug solution by adding SR48692, or another desired poorly soluble drug, to a system containing propylene glycol and aqueous sodium hydroxide; optionally adding this solution to an aqueous xylitol solution; and b) adding the drug solution to a seed powder, such as xylitol, dicalcium phosphate dihydrate, or a combination of lactose monohydrate and microcrystalline cellulose by spraying the drug solution on the seed powder.

Concentrated Solutions IIA and IIB

IIA We have discovered, as disclosed in prior application Ser. No. 08/808,761, that SR48692, or other poorly soluble drug, may be incorporated as the active ingredient in polyethylene glycol (PEG), NaOH, and $H_2O$ wherein the mole equivalent of NaOH per mole equivalent of the active ingredient is at least 1.0.

The formulations were prepared by adding aqueous NaOH to the polyethylene glycol. The active ingredient SR48692 was added to the PEG-NaOH until a solution is formed. Alternatively, the active ingredient was dispersed in the PEG with mixing. The NaOH solution was added resulting in dissolution of the active ingredient. Thereafter, the solution formulations were encapsulated in a soft gelatin capsule according to techniques known in the art in order to form a pharmaceutical dosage form.

IIB) During further research we have discovered that polyethylene glycol may be replaced with propylene glycol wherein the process comprises the steps of:

a) adding aqueous NaOH to propylene glycol;

b) adding SR48692, or another poorly soluble organic acid drug, to the aqueous NaOH/propylene glycol to form a solution of the active drug; and c) encapsulating of the solution in a soft gelatin capsule.

Alternatively, the active drug can be dispersed in propylene glycol first with mixing followed by the addition of aqueous NaOH to dissolve the active drug.

Yet another embodiment of the invention includes a pharmaceutical formulation comprising:

a poorly soluble drug, propylene glycol, NaOH, and water, wherein the mole equivalent of NaOH per mole equivalent of the poorly soluble drug is at least 1.1.

Suspensions IIIA and IIIB

IIIA) We have now discovered, as disclosed in prior application Ser. No. 08/810,559, that SR48692, or other poorly soluble drugs, may be incorporated as the active ingredient in a solvent system to produce a highly concentrated suspension suitable for hard gelatin capsule filling.

The suspension comprises:

0.1 to 40% by weight of SR48692;

0.1 to 40% by weight of Transcutol;

0.1 to 99% by weight starch;

NaOH; and $H_2O$.

The suspension can be prepared by adding the SR48692 to the solvent Transcutol, optionally in combination with PEG. The SR48692 is then dissolved by adding aqueous NaOH. The suspension is obtained by adding water, which causes a controlled precipitation. Addition of starch to the suspension permits the formulation to be filled into hard gelatin capsules preserving the integrity of the capsule shells.

IIIB) During fuirther research we have discovered that Transcutol may be replaced with propylene glycol in the suspension to produce a highly concentrated suspension suitable for hard gelatin capsule filling.

The suspension comprises:

0.1 to 40% by weight of SR48692;

0.1 to 40% by weight of propylene glycol;

0.1 to 99% by weight starch;

NaOH; and

H$_2$O.

Starch may be replaced with other diluents, such as microcrystalline cellulose and lactose.

In a further aspect, the invention relates to a method for preparing the sodium salt of a poorly soluble organic acid drug for use in solid formulations. The method comprises (a) bringing a poorly soluble organic acid drug, such as SR48692, into intimate contact with a conversion aid to provide a drug/aid mix;

(b) adding a concentrated aqueous solution containing greater than one equivalent of sodium hydroxide to the drug/aid mix; and (c) mixing the sodium hydroxide and drug/aid mix until the drug is greater than 95% in the form of its sodium salt. The conversion aid is chosen from the group consisting of PEG, mannitol and polysorbate, and the method allows conversion of the poorly soluble organic acid drug into its sodium salt substantially in the solid phase. Preferred conversion aids are PEG 400, mannitol and polysorbate 20. When the conversion aid is from 5 to 35% mannitol, it is preferred to add from 1.001 to 1.15 equivalents of sodium hydroxide. When the conversion aid is from 0.5 to 15% polysorbate 20, it is preferred to add from 1.001 to 1.1 equivalents of sodium hydroxide. When the conversion aid is from 2 to 60% PEG 400, it is preferred to add from 1.001 to 1.1 equivalents of sodium hydroxide. Since the drug substance is to be prepared in a solid dosage form, the amount of liquid employed in the conversion of the acid to the sodium salt is optimally kept to the smallest quantity possible. Therefore, concentrated solutions of NaOH (i.e. 15% to 35%) are preferred. The presence of the conversion aid allows the conversion to take place without complete dissolution of the acid (starting material) or salt (product). Thus the mixture passes from a thick paste to a thin paste and back to a thicker paste during reaction, but the reaction is never entirely in a liquid phase. The term "substantially in the solid phase" refers to this phenomenon, in which the viscosity of the reaction mixture remains above the viscosity of the conversion aid.

After conversion to the sodium salt, the mixture may be further processed by (c) adding sufficient water to prepare a slurry;

(d) adding excipients to form a wetted powder; and (e) drying to less than 15% by wt water.

The resulting solid may be formed into a tablet or filled into a capsule.

In another aspect the invention relates to particular formulations of SR 48692 made by the foregoing process. One embodiment is a pharmaceutical formulation comprising: (a) from about 40 parts by weight to about 60 parts by weight of the sodium salt of SR48692; (b) from 2 parts to about 60 parts by weight polyethylene glycol of molecular weight 200–800; and (c) less than 15 wt % water. In a preferred embodiment, the polyethylene glycol has a nominal molecular weight of 400, and it constitutes from 3 parts by weight to about 45 parts by weight, most preferably from 3 parts by weight to about 10 parts by weight. An embodiment is a pharmaceutical formulation comprising: (a) from about 40 wt % to about 60 wt % of the sodium salt of SR48692; (b) from 2 wt % to about 60 wt % polyethylene glycol of molecular weight 200–800; and (c) less than 15 wt % water.

In another embodiment, the pharmaceutical formulation comprises: (a) from about 40 parts by weight to about 60 parts by weight of the sodium salt of SR48692; (b) from 5 parts by weight to about 35 parts by weight mannitol; and (c) less than 15 wt % water. In a preferred embodiment, the mannitol constitutes from 7 parts by weight to about 24 parts by weight, most preferably from 8 parts by weight to about 15 parts by weight . An embodiment comprises (a) from about 40 wt % to about 60 wt % of the sodium salt of SR48692; (b) from 5 to 35 wt % mannitol; and (c) less than 15 wt % water.

In another embodiment the pharmaceutical formulation comprises: (a) from about 35 parts by weight to about 55 parts by weight of the sodium salt of SR48692; (b) from 0.5 parts by weight to about 15 parts by weight polysorbate 20; and (c) less than 15 wt % water. In a preferred embodiment, the polysorbate constitutes from 0.8 parts by weight to about 10 parts by weight, most preferably from 1 part by weight to about 5 parts by weight. An embodiment comprises (a) from about 35 wt % to about 55 wt % of the sodium salt of SR48692; (b) from 0.5 to 15 wt % polysorbate 20; and (c) less than 15 wt % water.

The first of the foregoing compositions may be expressed in product-by-process terms as a pharmaceutical formulation comprising: (a) from about 40 parts by weight to about 60 parts by weight of the reaction product of SR48692 with at least 1.0 equivalent of NaOH; (b) from 2 parts by weight to about 60 parts by weight polyethylene glycol of molecular weight 200–800; and (c) less than 15 wt % water. The second comprises:(a) from about 40 parts by weight to about 60 parts by weight of the reaction product of SR48692 with at least one equivalent of NaOH; (b) from 5 parts by weight to about 35 parts by weight mannitol; and (c) less than 15 wt % water. The third comprises: (a) from about 35 to about 55 parts by weight of the reaction product of SR48692 with at least one equivalent of NaOH; (b) from 0.5 parts by weight to about 15 parts by weight polysorbate 20; and (c) less than 15 wt % water.

All of the foregoing embodiments may be used to fill hard gelatin capsules or compressed into tablets.

In all of the foregoing descriptions of embodiments of the formulation, the ratios of SR48692:conversion aid:sodium hydroxide are distinguishing parameters. When capsules and tablets employing the formulations in high concentration with respect to other excipients are prepared, the percent by weight of the final dosage form will approximate the ratio of the SR48692 to conversion aid to sodium hydroxide. However, when capsules and tablets of lower potency (smaller amounts of active ingredient) are desired, the percent by weight of the SR48692, conversion aid and sodium hydroxide in the final dosage form will be significantly lower due to the presence of other excipients, but the ratio of the SR48692 to conversion aid to sodium hydroxide will remain.

DESCRIPTION OF THE PREFERRED EMBODIMENTS

Solid Dispersions IA and IB

IA) Transcutol is also known as diethyleneglycol monoethyl ether. In the dispersions of the invention, Transcutol is present in an amount of 0.1 to 30%, preferably 0.5 to 25% and most preferably, 1 to 20% by weight of the solid dispersion. Transcutol is commercially available and/or can be prepared by techniques well known to those skilled in the art.

Xylitol is a pentahydric alcohol derived from xylose having the structure $CH_2OH(CHOH)_3CH_2OH$ and a molecular weight of 152.1. In the dispersions of the invention, xylitol is present in an amount of 40 to 99.9%, preferably 45 to 99.5%, and most preferably 50 to 99% by weight of the solid dispersion. Xylitol is commercially available, and/or can be prepared by techniques well known to those skilled in the art.

In the dispersions of the invention, the drug substance is present in an amount of 0.1 to 60%. For some formulations, the drug is preferably 1 to 20% by weight of the solid dispersion. For others, particularly for hard capsule fills and for tablets, 35 to 60% is preferred. In a preferred embodiment the drug substance is SR48692.

SR48692

Extensive efforts have been made to formulate SR48692 into an acceptable solid dispersion. As described below, attempts to formulate this compound with conventional solid carriers such as high molecular weight polyethylene glycols did not yield satisfactory results.

The dispersions can be prepared by the steps of: dissolving the poorly soluble drug substance in Transcutol, optionally in the presence of a strong base such as NaOH or KOH, and adding the solution to xylitol to form a crystalline dispersion. The strong base is preferred when the acid form of the drug substance is employed. Up to 1 or more equivalents of base per equivalent of drug substance can be employed. In the final dispersion, the drug substance can be either in a crystalline state or amorphous depending on the drug substance selected and the drug concentration.

The following examples further illustrate the invention.

Examples 1–4

Preparation of Solid SR48692 Dispersions and Comparative Examples A–D

The formation of a solution by dissolving SR48692 in a basic solvent system was the initial step. SR48692 was dissolved in PEG 400 or Transcutol (diethyleneglycol monoethyl ether available from Gattefosse) with the addition of aqueous sodium or potassium hydroxide at approximately stoichiometric levels with SR48692. Concentrated aqueous sodium hydroxide (35% w/v) or potassium hydroxide (45% w/v) was added to a suspension of SR48692 in the organic solvent Transcutol available from Gattefosse; dissolution occurred in less than 15 minutes. Initially, preparations were formed using sodium hydroxide as the base, however, in later formulations potassium hydroxide was used. The basic solution was then added to molten PEG 8000 or xylitol at various levels to produce dispersions at final drug concentration up to approximately 9%. After addition of the SR48692 solution to the carrier, the system was mixed for approximately 2 minutes, then allowed to crystallize overnight at 20° C. Listed below are the combinations which were investigated:

| Example | Solvent | Carrier | Approx. Drug Conc. (% w/w) |
|---|---|---|---|
| 1 | Transcutol/NaOH | Xylitol | 3% |
| 2 | Transcutol/NaOH | Xylitol | 5% |

-continued

| Example | Solvent | Carrier | Approx. Drug Conc. (% w/w) |
|---|---|---|---|
| 3 | Transcutol/KOH | Xylitol | 8% |
| 4 | Transcutol/NaOH | Xylitol | 8% |
| A | Transcutol/NaOH | PEG 8K | 3% |
| B | PEG 400/NaOH | Xylitol | 5% |
| C | PEG 400/NaOH | PEG 8K | 5% |
| D | PEG 400/KOH | Xylitol | 8% |

HPLC results were obtained for measurement of potency as well as to check the impurity levels. The column used was a C18 column with a mobile phase consisting of 0.01M potassium phosphate monobasic (pH=2.5)/acetonitrile (270/730) at a flowrate of 1.0 ml/min. Injection volume was 10 microliters and the detection method was by UV (at 230 um). The instrument utilized throughout the study was a Hewlett Packard 1050 system. For the assay determination, the samples were first diluted in methanol/ammonium hydroxide (99.8/0.2), then further diluted in methanol to obtain a final SR48692 concentration of 0.04 mg/ml. For the impurity profile, the samples were diluted to a final SR48692 concentration of 1.0 mg/ml by the same procedure. The known impurities were quantitated versus external standards at a concentration of 0.0005 mg/ml. Any unknown impurities were quantified versus an external standard. All impurities greater than 0.01% were added to obtain the total impurity result.

Differential scanning calorimetry (DSC) scans were performed on the Perkin Elmer System-7 at 10° C./min heating rate from 25–125° C. under nitrogen purge. Approximately 5 mg samples were encapsulated in aluminum pans. The instrument was calibrated with indium (melting point 156.6° C.) and tin (melting point 231.9° C.) prior to use.

The dissolution rates of 25 mg SR48692 solid dispersions in hard gelatin capsules were measured in deionized water (900 ml, pH=5.5, unbuffered) at 37° C. A USP dissolution system (Apparatus 2) with a paddle speed of 100 RPM was used. Dissolution rate was monitored by UV (Hewlett Packard 8452A) at 234 nm. The pH was found to be relatively unchanged at the final concentrations (approximately 0.03 mg/ml).

A moisture absorption system was used to investigate the hygroscopicity of a batch of solid dispersion with acceptable impurity levels. The system was run from 5–80% RH in 5% steps at 25° C. The samples were purged at 50° C. and about 0% RH prior to analysis.

The xylitol/Transcutol formulations containing approximately 8% drug were analyzed with a powder x-ray diffraction system in order to determine whether the drug exists in a crystalline or a molecularly dispersed state within the dispersion. Samples were scanned at 2 degrees (2-theta)/minute and compared with pure xylitol. The system was run using Cu k-alpha radiation at 45 kv/40 ma and a liquid nitrogen cooled solid state germanium detector.

The results obtained for total impurity level and the assay for solid dispersions with PEG 8000 or xylitol as the carrier in combination with Transcutol or PEG 400 as the solvent are shown in Table 1.

TABLE 1

Summary of HPLC RESULTS

| Example | % Impurity | Assay (%) | Nominal Conc. (%) |
|---|---|---|---|
| A | 28.0 | 2.1 | 3 |
| 1 | 0.74 | 2.8 | 3 |
| 2 | 0.40 | 5.2 | 5 |
| B | 1.4 | 5.1 | 5 |
| C | 4.5 | 4.8 | 5 |
| 3 | 0.55 | 9.4 | 8 |
| D | 19.2 | 6.6 | 8 |
| 3 | 0.42 | 8.6 | 8 |
| 3 | 0.36 | 8.8 | 8 |

The total batch size for these samples was about 10 g. At approximately 3% drug concentration, the use of PEG 8000 with Transcutol resulted in gross degradation as reflected in the high total impurity level and the lower assay value (Example A). In contrast, the combination of xylitol with Transcutol produced a formulation with a significantly lower total impurity level of 0.74% (Example 1).

At approximately 5% drug concentration, the combination of xylitol as the carrier with Transcutol as the solvent again produced an acceptable impurity level of 0.40% (Example 2). The total impurity levels for the xylitol/PEG 400 (Example B) and the PEG 8000/PEG 400 (Example C) were 1.4% and 4.5% respectively. Acceptable impurity levels in the final product should approximate impurity levels present in the starting materials. It appeared that the use of PEG 8000 as the carrier or PEG 400 as the solvent resulted in high impurity levels. The carrier/solvent combination of xylitol/Transcutol demonstrated unexpectedly lower impurity levels compared to xylitol/PEG.

At high drug concentrations (approximately 8–9%), the use of potassium hydroxide versus sodium hydroxide was shown to result in equally low levels of impurity (Example 3). The average impurity level for three 10 gram batches with KOH were 0.44+/−0.10%. As was observed previously, the use of PEG 400 as the solvent resulted in unacceptable degradation (19.2% total impurity, Example D).

HPLC data for two batches of approximately 100 g made with xylitol as the carrier, Transcutol as the solvent and either potassium or sodium hydroxide as the base exhibited low impurity levels; 0.30% (Example 3) and 0.27% (Example 4) total impurities were observed for the KOH and NaOH based systems, respectively.

Differential scanning calorimetry (DSC) scans obtained at 10° C./min for the batches evidenced that the effect of the formulation components on the melting behavior of xylitol is surprisingly low. The melting peak of the KOH based formulation (Example 3) was 89.4° C., a depression of 8.7 degrees. Similarly, the melting peak of the NaOH formulation (Example 4) was 96.3° C., a depression of only 1.8 degrees. X-ray powder diffraction patterns of the formulation indicated a predominantly crystalline xylitol phase.

A screening dissolution test was run in USP Apparatus 2 with water at pH 5.5 (unbuffered) at 37° C. comparing the solid dispersion of this invention (Example 2) with unformulated (jet-milled) SR48692. The solid dispersions provide enormous dissolution enhancement with respect to pure drug and low impurity levels (0.4%). The fraction dissolved was well over 90% in 10 minutes; in contrast, the capsules containing SR48692 drug substance (unformulated) did not reach 10% dissolved at the end of the experiment of 60 minutes. Dissolution experiments incorporating the solid dispersion at 25 mg/capsule (Example 2) at pH 7.0 (37° C.) with 0.5% sodium lauryl sulfate as the dissolution medium also showed rapid dissolution, with more than 90% dissolved after 10 minutes.

The hygroscopicity of a solid dispersion based formulation (Example 3) was screened by running a sample at 25° C. from 5–80% RH in 5% steps. The data showed relatively low (~1%) moisture uptake at 25° C. below 60% RH; this level would be acceptable for a solid formulation. Hysteresis data showed the moisture uptake at 80% RH was reversible; as the RH was decreased back down to 5%, the moisture was not retained.

The x-ray powder diffraction patterns of the xylitol/Transcutol formulations (Examples 3–4) compared with pure xylitol suggest that the dispersion appears to be a "crystalline" dispersion rather than an amorphous dispersion/solid solution. This hypothesis was confirmed by hot-stage microscopy. It appears that the xylitol/Transcutol/base formulation has high dissolution rates despite the existence of the drug in a crystalline state. The explanation for this observation is that the crystalline state is likely the salt form rather than the acid form.

The formulation of solid dispersions at dosages up to 40 mg/capsule containing xylitol/Transcutol/NaOH (or KOH) were shown to have acceptable impurity levels (typically <0.5%) and rapid dissolution (>90% in 10 minutes) in water at 37° C. (pH=5.5). Analysis by differential scanning calorimetry and x-ray powder diffraction indicated the existence of crystalline xylitol and crystalline drug. The crystalline nature of the drug was confirmed by observation of the formulation with polarized light microscopy at the melting temperature of xylitol. FTIR analysis of the solid produced when adding the solid dispersion formulation to 0.1N HCl indicated a desirable amorphous acid phase. This suggests that the solid dispersion could have similar bioavailability when compared to the liquid. Advantages of the dispersion formulation include improved manufacturability and ease of fill into hard gel capsules.

Naproxyn

Another preferred poorly soluble drug substance is Naproxyn. The formulation of Naproxyn was prepared by dissolving 4.6 g of Naproxyn in 4.6 g of Transcutol (diethylene glycol monoethyl ether) with the addition of 2 g of 45% w/v aqueous potassium hydroxide. The Naproxyn dissolved within a few minutes of adding the basic solution. The Naproxyn solution was then added to molten xylitol at 100° C. at a ratio of approximately 1:3 by weight. The product was mixed for several minutes, then poured into a crystallizing dish at room temperature. After 24 hours, the product was removed and ground in a mortar and pestle. The final Naproxyn concentration was approximately 10% by weight. The product was a white crystalline powder with a melting point of approximately 90° C.

The dissolution rate using USP Apparatus 2 of the Naproxyn solid dispersion formulation (filled into size 0 hard gelatin capsules) was compared with pure Naproxyn and the potassium salt of Naproxyn under the following conditions:

Dissolution media—0.01 M phosphate buffer, pH=6

Volume—1000 ml RPM—50

Dosage—50 mg active for formulation, Naproxyn and Naproxyn potassium salt

Temperature—37° C.

The dissolution results (3 capsules/formulation) are summarized below:

| Formulation | % Dissolved at 30 minutes |
| --- | --- |
| Xylitol Dispersion of Naproxyn Potassium | 97.4 ± 0.8 |
| Naproxyn | 57.1 ± 18.5 |
| Naproxyn Potassium | 98.3 ± 1.0 |

The formulation in the capsules containing the xylitol dispersions dissolved faster than the capsules containing Naproxyn drug substance. The formulation in the capsules containing the potassium salt of Naproxyn dissolved in a similar manner to the xylitol based formulation.

The advantage of the xylitol/Transcutol/base dispersion versus a formulation containing the acid form of a drug is to cause partial or complete conversion to the salt which will, in general, enhance dissolution rate and solubility. The advantage of the xylitol dispersion versus a formulation containing the salt form is to avoid the potential problems involved with storage of salts (e.g., hygroscopicity). There are several advantages of using xylitol specifically as a carrier. It crystallizes well despite the inclusion of 20% or more drug and Transcutol. The melting point (95° C.) is higher than polyethylene glycols (50–60° C.) and there appears to be little melting point depression for xylitol dispersions. In addition, it is highly water soluble, resulting in rapid dissolution and drug release.

IB) The Spray Granulation Process

Materials used

SR48692

Xylitol

Lactose Monohydrate

Microcrystalline Cellulose

Dicalcium Phosphate

Croscarmellose Sodium

Sodium Stearyl Fumarate

Magnesium Stearate

Silicon Dioxide

Propylene Glycol

NaOH

Preparation of Feed Spray

A drug solution was prepared by adding SR48692 to a solvent system containing propylene glycol and aqueous sodium hydroxide in a solvent/drug ratio of about 1.2:1 at a temperature of about 40° C. The sodium hydroxide level was in slight excess relative to drug, i.e. about 1.1:1 molar ratio. The system was mixed for approximately 30 to 60 minutes to insure proper dissolution of the drug. After dissolution was complete, the SR48692 solution was added to a 50% w/w aqueous xylitol solution and mixed for about 10 minutes at about 25° C. The final SR48692 concentration in the spray solution was approximately 8% w/w.

Fluid Bed Processing

A fluid bed processor was utilized to produce all products. Seed powder was added to the unit and preheated to 40–45° C. over a 15 minute period. Seed powders included xylitol, dicalcium phosphate, and lactose monohydrate combined with microcrystalline cellulose. Approximately 700 g of seed powder was used. The drug solution was sprayed onto the seed powder at the following conditions:

| Aeromatic Fluid Bed Parameters | |
| --- | --- |
| Parameters | Setting |
| Spray Rate | 4 cc/min |
| Inlet Air Temp | 60° C. |
| Product Temp | 40–45° C. |
| Atomization Air Pressure | 1 Bar |
| Air Flow | 40 CMH |

Example 5 illustrates the invention.

Example 5

| Feed Spray | | Seed Powders |
| --- | --- | --- |
| SR48692 | 20 g | Xylitol |
| Propylene Glycol | 24 g | Lactose Monohydrate |
| NaOH (35% w/v aq) | 6 g | Dicalcium Phosphate |
| Xylitol | 100 g | Microcrystalline Cellulose |
| Purified Water | 100 g | |

Addition of Excipients for Tablet/Capsule Formulation

The product containing xylitol as the seed powder was preground with a glass mortar and pestle and screened through a 200 mesh screen prior to adding additional excipients. This product was modified by the addition of 9% microcrystalline cellulose, 0.5% silicon dioxide as glidant, and a lubricant such as 2% w/w sodium stearyl fumarate or 2% w/w magnesium stearate. The product which was prepared by using lactose monohydrate/microcrystalline cellulose in the ratio of 6:1 as the seed powder was modified by dry blending 2% croscarmellose sodium as disintegrant, and 1% sodium stearyl fumarate as the lubricant. The product which was prepared with dicalcium phosphate dihydrate was modified by dry blending 10% corn starch and 4% w/w croscarmellose as a disintegrant.

The product was pressed into tablets or filled into capsules.

Testing for Impurity

HPLC results were obtained for measurement of impurity levels, The column used was a C18 column with a mobile phase consisting of 0.01M potassium phosphate monobasic (pH=2.5)/acetonitrile (270/730) at a flowrate of 1.0 ml/min. Injection volume was 10 microliters and the detection method was by UV (at 230 nm). For the assay determination, the samples were first diluted in methanol/ammonium hydroxide (99.8/0.2), then further diluted in methanol to obtain a final SR48692 concentration of 1.0 mg/ml. The known impurities were quantitated versus external standards at a concentration of 0.0005 mg/ml. Any unknown impurities were quantified versus an external standard. All impurities greater than 0.01% were added to obtain the total impurity result.

| Seed Powder | Solvent | % Impurity |
| --- | --- | --- |
| Xylitol* | Propylene Glycol | 0.6% |
| Xylitol* | Propylene Glycol | 0.6% |
| Dicalcium. Phosphate Dihydrate* | Propylene Glycol | 0.7% |
| Lactose MH/Microcryst. Cellulose* | Propylene Glycol | 0.5% |

-continued

| Seed Powder | Solvent | % Impurity |
|---|---|---|
| Lactose MH/Microcryst. Cellulose** | Propylene Glycol | 0.3% |
| Lactose MH/Microcryst. Cellulose** | Propylene Glycol | 0.3% |

*Initial drug impurity level = 0.6%
**Initial drug impurity level = 0.3%

Dissolution Screening

The dissolution rate of 10 mg tablets and capsules was measured in pH=7 phosphate buffer (0.005 molar) at 37° C. A Distek USP dissolution system was used with a paddle speed of 75 RPM. Dissolution rate was monitored by UV (Hewlett Packard 8452A) at 260 mn with background correction at 480 mn. The results reported are the average of 2–3 tablets for each formulation.

Effect of Seed Powder on Dissolution Rate 10 mg Tablets, 75 RPM, pH=7 buffer (0.0005M phosphate)

| | % Dissolved | | |
|---|---|---|---|
| Time (min) | Lactose/Microcrystalline Cellulose | Xylitol | Dicalcium Phosphate |
| 7.5 | 85% | 69% | 21% |
| 15 | 100% | 95% | 28% |
| 22.5 | 100% | 96% | 39% |
| 30 | 100% | 97% | 55% |

Concentrated Solutions IIA and IIB

IIA) In accordance with this invention, there is provided a pharmaceutical formulation comprising SR48692 as the active ingredient, polyethylene glycol, NaOH, and $H_2O$, the mole equivalents of NaOH per mole equivalent of agent is at least about 1.0, preferably 1.05 or greater.

The polyethylene glycol used herein has an average molecular weight of between about 200–100,000 daltons (hereinafter, all molecular weights are expressed in daltons). Moreover, when sufficient PEG is employed to prepare solutions, the molecular weight of polyethylene glycol selected affects the type of solution produced. Polyethylene glycol having an average molecular weight from about 200–800, preferably from about 300–700, and most preferably about 400, produces a soft gelatin capsule fill solution that is a liquid. Polyethylene glycol having an average molecular weight from about 800–10,000, preferably from about 2,000–8,000, produces a soft gelatin capsule fill solution that is semisolid, and polyethylene glycol having an average molecular weight between about 10,000–100,000, preferably about 15,000–60,000, produces a soft gelatin capsule fill solution that is solid. The person of skill will recognize that substantially reducing the amounts of solvent (PEG) will result in considerably different physical properties.

Contemplated equivalents of polyethylene glycol include analogs, such as the polyethylene glycol ethers of various alcohols including but not limited to tetraglycol—the polyethylene glycol ether of tetrahydrofurfuryl alcohol, and copolymers of polyethylene glycol.

The polyethylene glycol can be present in amounts of 60–99%, preferably 70–98% and more preferably 80–95% by weight based on the total weight of the formulation.

The formulation can comprise 0.1–25%, preferably 0.5–20% and more preferably 1–15% by weight water.

For solutions, the SR48692 can be present in an amount up to 10%, preferably 0.1–9% and more preferably 0.5–7.5% by weight.

In solutions, the mole equivalents of NaOH present per mole of SR 48692 is preferably at least about 1.1, preferably at least 1.2 and most preferably at least 1.3. Inadequate solubility of the agent was found at mole equivalents of 1.0 and less.

The formulations of this invention can be prepared by adding aqueous NaOH to the polyethylene glycol. The active ingredient SR48692 is added to the PEG-NaOH until a solution is formed. Alternatively, the active ingredient can be dispersed in the PEG with mixing. Thereafter, the NaOH solution can be added resulting in dissolution of the active ingredient. The solution formulations can be encapsulated in a soft gelatin capsule according to techniques known in the art in order to form a pharmaceutical dosage form.

The following examples further illustrate the invention.

Example 6

A 2.02 kg quantity of a 0.5% w/v sodium hydroxide solution was added to 20.4 kg of polyethylene glycol 400; this mixture was stirred until a clear solution was formed. To the polyethylene glycol 400/sodium hydroxide solution was added 100 g of SR48692; this mixture was stirred until the drug was completely dissolved by visual inspection. The resulting SR48692 solution was shipped to R. P. Scherer for encapsulation into soft gelatin capsules.

Example 7

A 1.98 kg quantity of a 2.5% sodium hydroxide solution was added to 20.0 kg of polyethylene glycol 400; this mixture was stirred until a clear solution was formed. To the polyethylene glycol 400/sodium hydroxide solution was added 600 g of SR48692; this mixture was stirred until the drug was completely dissolved by visual inspection. The resulting SR48692 solution was shipped to R. P. Scherer for encapsulation into soft gelatin capsules.

Example 8

A 1.92 kg quantity of a 6.0% w/v sodium hydroxide solution was added to 19.4 kg of polyethylene glycol 400; this mixture was stirred until a clear solution was formed. To the polyethylene glycol 400/sodium hydroxide solution was added 1.50 kg of SR48692; this mixture was stirred until the drug was completely dissolved by visual inspection. The resulting SR48692 solution was shipped to R. P. Scherer for encapsulation into soft gelatin capsules.

| Ingredient | Composition mg/capsule |
|---|---|
| SR48692 CAPSULE SOFT GELATIN 5MG | |
| Polyethylene Glycol 400 | 1020 |
| Sodium Hydroxide | 0.500 |
| Purified Water | 100 |
| SR48692 | 5 |
| Soft Gelatin Capsule, White Opaque | |
| R.P. Scherer Capsule | |
| 18 Oblong (Die Size W18BD) | |
| Gel Formula 005LSMH | |
| Color 911 P | 1 Capsule |

-continued

| Ingredient | Composition mg/capsule |
|---|---|
| SR48692 CAPSULE SOFT GELATIN 5MG | |
| SR48692 CAPSULE SOFT GELATIN 30MG | |
| Polyethylene Glycol 400 | 1000 |
| Sodium Hydroxide | 2.50 |
| Purified Water | 96.4 |
| SR48692 | 30 |
| Soft Gelatin Capsule, White Opaque | |
| R.P. Scherer Capsule | |
| 18 Oblong (Die Size W18BD) | |
| Gel Formula 005LSMH | |
| Color 911 P | 1 Capsule |
| SR48692 CAPSULE SOFT GELATIN 75MG | |
| Polyethylene Glycol 400 | 969 |
| Sodium Hydroxide | 5.77 |
| Purified Water | 90.4 |
| SR48692 | 75 |
| Soft Gelatin Capsule, White Opaque | |
| R.P. Scherer Capsule | |
| 18 Oblong (Die Size W18BD) | |
| Gel Formula 005LSMH | |
| Color 911 P | 1 Capsule |

IIB) In accordance with this embodiment of the present invention, the pharmaceutical formulations comprises a poorly soluble organic acid drug selected from the group consisting of: analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, bete-adrenoceptor blocking agents, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, anoretics, sympathomimetics, thyroid agents, vasodilators and xanthines; propylene glycol; NaOH and water, wherein the mole equivalent of NaOH per mole equivalent of the poorly soluble drug is at least about 1.1.

Preferred drugs are SR48692 and Naproxyn.

The so-produced drugs are filled into soft gelatin capsules.

Example 9

| SR48692 CAPSULE SOFT GELATIN 5MG | |
|---|---|
| Ingredient | Composition mg/capsule |
| Propylene Glycol | 1020 |
| Sodium Hydroxide | 0.500 |
| Purified Water | 100 |
| SR48692 | 5 |
| Soft Gelatin Capsule, White Opaque | |
| R.P. Scherer Capsule | |
| 18 Oblong (Die Size W18BD) | |
| Gel Formula 005LSMH | |
| Color 911 P | 1 Capsule |

Example 10

| SR48692 CAPSULE SOFT GELATIN 30MG | |
|---|---|
| Ingredient | Composition mg/capsule |
| Propytene Glycol | 1000 |
| Sodium Hydroxide | 2.50 |
| Purified Water | 96.4 |
| SR48692 | 30 |
| Soft Gelatin Capsule, White Opaque | |
| R.P. Scherer Capsule | |
| 18 Oblong (Die Size W18BD) | |
| Gel Formula 005LSMH | |
| Color 911 P | 1 Capsule |

Example 11

| SR48692 CAPSULE SOFT GELATIN 75MG | |
|---|---|
| Ingredient | Composition mg/capsule |
| Propylene Glycol | 969 |
| Sodium Hydroxide | 5.77 |
| Purified Water | 90.4 |
| Soft Gelatin Capsule, White Opaque | |
| R.P. Scherer Capsule | |
| 18 Oblong (Die Size W18BD) | |
| Gel Formula 005LSMH | |
| Color 911 P | 1 Capsule |

Suspensions IIIA and IIIB

IIIA) We have discovered a solvent system for SR48692 which produces a highly concentrated suspension of the active ingredient suitable for a hard gelatin capsule filling.

More specifically, there is provided a pharmaceutical formulation comprising:

0.1 to 40% by weight of SR48692;

0.1 to 40% by weight of Transcutol;

0.1 to 99% by weight starch;

NaOH; and $H_2O$.

The SR48692 can be present in an amount up to 40%, preferably 0.1–35% and more preferably 0.5–30% by weight.

The Transcutol is present in an amount of 0.1 to 40%, preferably 0.5 to 35% and most preferably, 1 to 30% by weight of the solid dispersion. Transcutol is commercially available and/or can be prepared by techniques well known to those skilled in the art.

The starch can be present in an amount of 0.1–99% by weight. Starches which have previously been used in pharmaceutical formulations are preferred for use herein. The starch can be pre-gelatinized, i.e., chemically and/or mechanically processed to rupture all or part of the granules in the presence of water and subsequently dried. Suitable USP/NF starches are described in the Handbook of Pharmaceutical Excipients, Second Edition published jointly by the American Pharmaceutical Association and the Pharmaceutical Society of Great Britain, The Pharmaceutical Press, 1994. A preferred starch is Starch 1500, commercially available from Colorcon.

The suspension can comprise 0.1–20%, preferably 0.5–15% and more preferably 1–13% water. Higher amounts of water tend to soften and/or dissolve the gelatin capsules shells.

The NaOH is present in an amount such that the mole equivalents of NaOH per mole equivalent of SR48692 is from about 0.5 to 1.5.

The polyethylene glycol can be present in amounts of 0–90%, preferably 1–85% and more preferably 2–80% by weight based on the total weight of the formulation.

The polyethylene glycol optionally used herein has an average molecular weight of between about 200–100,000 daltons (hereinafter, all molecular weights are expressed in daltons). Moreover, the molecular weight of polyethylene glycol selected affects the type of solution produced. Polyethylene glycol having an average molecular weight from about 200–800, preferably from about 300–700, and most preferably about 400, produces a hard gelatin capsule fill solution that is a liquid. These low molecular weights are preferred because the PEG is miscible with the Transcutol. High molecular weights may disadvantageously require heat to melt and/or dissolve in the Transcutol. Polyethylene glycol having an average molecular weight from about 800–10,000, preferably from about 2,000–8,000, produces a hard gelatin capsule fill solution that is semisolid, and polyethylene glycol having an average molecular weight between about 10,000–100,000, preferably about 15,000–60,000, produces a hard gelatin capsule fill solution that is solid.

Contemplated equivalents of polyethylene glycol include analogs, such as the polyethylene glycol ethers of various alcohols including but not limited to tetraglycol—the polyethylene glycol ether of tetrahydrofurfuryl alcohol, and copolymers of polyethylene glycol.

In the examples, the conversion of the acid to the sodium salt does not occur except in the presence of the mannitol, polysorbate, propylene glycol, transcutol and PEG or xylitol. These materials, without which the conversion does not occur, we refer to as "conversion aids". We have found that in some instances, the treatment of the drug substance with a preformed mixture of NaOH and the conversion aid, while it may enable the chemical conversion to the sodium salt, results in a product that cannot be readily manipulated for formulation. In particular, rather than remaining a paste, the mixture hardens so that stirring, which is necessary for homogeneity, becomes impossible with simple equipment. This is unattractive for commercial production.

This problem can be overcome by adding the poorly soluble drug substance to the conversion aid and then adding aqueous NaOH. The mixture becomes viscous, but it remains a stirrable paste. A suspension is obtained by adding water, which causes a controlled precipitation. Other formulation aids, such as starch, microcrystalline cellulose and sodium starch glycolate may then be added to the suspension, which permits the formulation to be filled into hard gelatin capsules or compressed into tablets.

The following example further illustrates the invention.

Example 12

12 g of PEG 400 and 12 g of diethyleneglycol monoethyl ether (Transcutol) were mixed with a magnetic stir plate apparatus at 20° C. Next, 16 g of SR48692 were added along with 4.7 g of aqueous sodium hydroxide (35% w/v). The system was mixed at 20° C. which caused a large proportion of SR48692 to dissolve after 10 minutes. 4 g of purified water was then added and the system was mixed for several hours as a precipitate formed (until a concentrated suspension of drug was achieved). The product was mixed with 12 g of pre-gelatinized starch with a mortar and pestle to obtain the final formulation. The product was filled into size #0 hard gelatin capsules at 150 mg drug/capsule. After 8 months at room temperature the estimated total impurity level of the product was 0.4%, well within acceptable levels.

IIIB) In this embodiment of the present invention a pharmaceutical composition in the form of a suspension is provided for filling hard gelatin capsules comprising:

a) 0.1 to 40% by weight of SR48692;

b) 0.1 to 40% by weight propylene glycol;

c) 0.1 o 99% by weight of starch;

d) 0.1 to 20% water; and e) NaOH, wherein the mole equivalent of NaOH per mole equivalent of the poorly soluble drug is from 0.5 to 1.5.

Solid Suspensions IVA and IVB

We have discovered three solvent systems for SR48692 which produce a highly concentrated suspension of the active ingredient suitable for a hard gelatin capsule filling. The concentrated suspension appears suitable for processing into tablets as well. It is believed that these formulations will provide high bioavailability in a solid formulation, which has been previously unattainable. More specifically, the compositions employ mannitol, PEG or polysorbate as conversion aids. The ratios of SR48692 to conversion aid are higher than for other formulations, so as to facilitate use in the solid state without the need to remove liquid or add large volumes of excipients.

Example 13

| Component | Mg/capsule |
| --- | --- |
| SR48692 Milled | 60.xx |
| Sodium Hydroxide | 4.58 |
| Mannitol | 13.5x |
| Microcrystalline cellulose (Avicel PH101) | 31.1x |
| Corn Starch | 16.8x |
| Sodium starch glycolate (Explotab) | 7.05 |
| Size #2 Opaque White Capsule | 1 Ea |
| Theoretical Fill Weight | 133.xx |

Two hundred grams of SR48692 was loaded into a planetary mixer bowl and 225 g of a 20% aqueous mannitol solution was added. The mixture was mixed until all of the drug substance was visually wet, and 50.9 g of 30% aqueous sodium hydroxide solution was added to the mixture. The mixture was mixed until viscous and then 78.8 g of purified water was added in aliquots. The mixing bowl sides were scraped as needed and mixing was continued for 4½ hours following addition of all of the water. The mixture was transferred to a granulator and 23.5 g of sodium starch glycolate was added. The mixture was mixed until homogenous. A preblended mix of 104 g of microcrystalline cellulose and 55.9 g of cornstarch was added and mixed until granules formed. The granules were sized and dried to a final moisture content of 6% w/w. Number 2 hard gelatin capsules were filled to the weight shown in the table above.

Example 14

| Component | Mg/capsule |
| --- | --- |
| SR48692 Milled | 60.0x |
| Sodium Hydroxide | 4.27 |
| Polysorbate 20 (Tween 20) | 2.40 |

-continued

| Component | Mg/capsule |
|---|---|
| Microcrystalline cellulose (Avicel PH101) | 54.0x |
| Corn Starch | 29.9x |
| Sodium starch glycolate (Explotab) | 10.3x |
| Size #2 Opaque White Capsule | 1 Ea |
| Theoretical Fill Weight | 161.xx |

Two hundred grams of SR48692 was loaded into a planetary mixer bowl and 80 g of a 10% aqueous solution of polysorbate 20 was added. The mixture was mixed until all of the drug substance was visually wet, and 70.8 g of 20% aqueous sodium hydroxide solution was added to the mixture. The mixture was mixed until viscous and then 400 g of purified water was added in aliquots. The mixing bowl sides were scraped as needed and mixing was continued for 4½ hours following addition of all of the water. The mixture was transferred to a granulator and 34.3 g of sodium starch glycolate was added. The mixture was mixed until homogenous. A preblended mix of 180 g of microcrystalline cellulose and 99.7 g of cornstarch was added and mixed until granules formed. The granules were sized and dried to a final moisture content of 5% w/w. Number 2 hard gelatin capsules were filled to the weight shown in the table above.

Example 15

| Component | Mg/capsule |
|---|---|
| SR48692 Milled | 60.0x |
| Sodium Hydroxide | 4.25 |
| Polyethylene Glycol 400 (PEG 400) | 5.42 |
| Microcrystalline cellulose (Avicel PH101) | 33.8x |
| Corn Starch | 15.6x |
| Sodium starch glycolate (Explotab) | 7.79 |
| Size #2 Opaque White Capsule | 1 Ea |
| Theoretical Fill Weight | 127.xx |

Two hundred grams of SR48692 was loaded into a planetary mixer bowl and 90.5 g of a 20% aqueous solution of polyethylene glycol 400 was added. The mixture was mixed until all of the drug substance was visually wet, and 70.9 g of 20% aqueous sodium hydroxide solution was added to the mixture. The mixture was mixed until viscous and then 217 g of purified water was added in aliquots. The mixing bowl sides were scraped as needed and mixing was continued for 4½ hours following addition of all of the water. The mixture was transferred to a granulator and 25.9 g of sodium starch glycolate was added. The mixture was mixed until homogenous. A preblended mix of 112.6 g of microcrystalline cellulose and 51.9 g of cornstarch was added and mixed until granules formed. The granules were sized and dried to a final moisture content of 5% w/w. Number 2 hard gelatin capsules were filled to the weight shown in the table above.

The following Examples 16–19 illustrate processes falling outside the claims. These processes did not provide successful conversions, in the sense that they either did not convert or produced a salt that was difficult to manipulate for further formulation.

Example 16

Into a 20 cc glass vial was weighed 1.01 g of glycerol, and 1.0488 g of 20% w/w NaOH solution was added. The material was mixed on a vortex genie until visibly homogeneous. Three grams of milled SR 48692 was added a spatula at a time with stirring with a micro spatula. All drug could not be wetted with the amount of "liquid" phase present. An additional 0.4 g of glycerol was added. The "liquid" phase was still insufficient. Added a further 1. 1380 g of glycerol and mixed the mixture by hand with the micro spatula until all SR48692 was added and wetted. A paste resulted, which was placed in a Lightnin' mixer and mixed for 1 hour. The paste was spread onto a 4×4" weigh paper and labeled; then placed under hood. A small sample was used to perform FTIR, which indicated no conversion to the sodium salt.

Example 17

Into a 20 cc glass vial was weighed 1.01 g of glycerol and 1.0488 g of 20% w/w NaOH solution was added. The material was mixed on a vortex genie until visibly homogeneous. Two grams of milled SR 48692 was added a spatula at a time with stirring with a micro spatula. The mixture turned to a sticky dough consistency. The mixture was alternatively mixed by hand and Lightnin' mixer with a micro spatula. The mixture was mixed until formation of solid no longer allowed mixing to occur. (Approximately 1 hour.) The mixture was scraped onto a weigh boat, labeled and placed under the hood to allow air drying. FTIR confirmed conversion to Na salt.

Example 18

A 50 mL reaction beaker was fitted to a ring stand and circulating water tubing was connected. The water bath was initially set at 70° C. After the water bath was allowed to warm up for 30 minutes, the mixing propeller was attached to the Lightnin' mixer. Six grams of PEG3350 was transferred to the 50 mL reaction beaker and allowed to mix until melted, whereupon 3.97 g of 35% w/w NaOH solution was added to the molten PEG3350 and mixed for 3 minutes. Twenty grams of SR48692 was added to the molten PE3350/NaOH solution slowly, a spatula full at a time. As drug was added, the molten mixture began to solidify. A spatula was used to try to mix the viscous mixture. The mixture began to form granules before all drug was added. The mixture then became too "dry" to continue mixing. An additional 9.92 g of PEG3350 was added. The mixture then became more "pasty" and eventually after 5 minutes it was possible to add more drug. The mixture became more dry again after the drug addition. More PEG3350 was then added (8.60 g) and 1 gram of water. The mixture then became more liquid like a thick dough. The Lightnin' mixer was turned up and allowed to mix for 30 minutes, at which point the mixture became dry again, forcing the mixer to be stopped. The mixture was scooped out of the reaction beaker and spread into a weigh boat, placed into the refrigerator at 5° C. for 5 minutes then placed into a small coffee grinder and milled into granular powder. Although conversion from the acid to Na salt occurred, the product was extremely difficult to make. The reaction beaker wasn't able to keep the molten PEG3350 in the molten state during drug addition.

Example 19

Since the process of making Example 18 was very labor intensive, it was contemplated that perhaps using PEG 3350 with a 40% concentration and a higher water content would allow a more "liquid" state during mixing and salt conversion. The experiment was repeated with 6.5 g PEG 3350, 3.49 g of 20% NaOH (w/w) and 10 g of SR48692. The SR48692 was added slowly to allow wetting, but during last quarter of addition of SR48692 the mixture became very doughy, so 0.83 g of water was added to make mixture more "liquid" state. Mixed for 30 minutes (alternated between hand kneading with spatula and mixing with Lightnn' mixer. The speed was adjusted depending on how much was needed to mix the mixture, and the mixer was raised and lowered while mixing. The reaction was very difficult to mix, and the mixer was unable to readily mix the reaction. After refrigeration at 5° C. for 10 minutes, the mixture was broken into pieces, ground in a coffee grinder and mixed to powder. FTIR confirmed Na salt conversion, but mixing remained a serious obstacle in terms of processing.

Having described the invention with reference to its preferred embodiments, it is to be understood that modifications within the scope of the invention will be apparent to those skilled in the art

What is claimed is:

1. A pharmaceutical formulation in the form of a solid dispersion comprising:
   a) a poorly soluble organic acid drug substance selected from the group consisting of: analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, anoretics, sympathomimetics, thyroid agents, vasodilators and xanthines;
   b) propylene glycol;
   c) a sufficient quantity of a solid diluent selected from the group consisting of xylitol, dicalcium phosphate dihydrate, and lactose monohydrate/microcrystalline cellulose to provide a solid dispersion.

2. The pharmaceutical formulation of claim 1 wherein said drug substance is SR48692.

3. The pharmaceutical formulation of claim 1 further comprising a base.

4. The pharmaceutical formulation of claim 1 wherein said drug substance is Naproxyn.

5. The pharmaceutical formulation of claim 4 further comprising a base.

6. The pharmaceutical formulation of claim 1 further comprising a base.

7. A process of preparing a pharmaceutical formulation in the form of a solid dispersion comprising the steps of:
   a) dissolving a poorly soluble organic acid drug substance in aqueous sodium hydroxide/propylene glycol mixture to form a solution wherein said poorly soluble drug substance is selected from the group consisting of: analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, anoretics, sympathomimetics, thyroid agents, vasodilators and xanthines; and
   b) adding the solution to a sufficient quantity of a solid diluent selected from the group consisting of xylitol, dicalcium phosphate dihydrate, and lactose monohydrate and/or microcrystalline cellulose to provide a solid dispersion.

8. The process of claim 7 further comprises adding water or aqueous xylitol to said sodium hydroxide/propylene glycol mixture in step (a).

9. The process of claim 7 wherein said drug substance is SR48692.

10. The process of claim 7 wherein said drug substance is Naproxyn.

11. A concentrated drug solution for soft gelatin capsule filling consisting essentially of:
    a) a poorly soluble organic acid drug selected from the group consisting of analgesics, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, prostaglandins, radio-pharmaceuticals, sex hormones, anti-allergic agents, stimulants, anoretics, sympathomimetics, thyroid agents, vasodilators and xanthines;
    b) propylene glycol;
    c) sodium hydroxide; and
    d) water;
wherein the mole equivalent of sodium hydroxide per mole equivalent of the poorly soluble drug is at least 1.1.

12. The concentrated drug solution of claim 11 wherein said poorly soluble drug is SR48692.

13. The concentrated drug solution of claim 12 wherein the ratio of mole equivalents of sodium hydroxide per mole equivalent of SR48692 is at least 1.2.

14. The concentrated drug solution of claim 11 wherein said poorly soluble drug is Naproxyn.

15. The concentrated drug solution of claim 14 wherein the ratio of mole equivalents of sodium hydroxide per mole equivalent of Naproxyn is at least 1.2.

16. The concentrated drug solution of claim 11 wherein the ratio of mole equivalents of sodium hydroxide per mole equivalent of said poorly soluble drug is at least 1.2.

17. A pharmaceutical formulation in a highly concentrated suspension form for a hard gelatin capsule filling comprising:

0.1 to 40% by weight of SR48692;
0.1 to 40% by weight propylene glycol;

0.1 to 99% by weight of a diluent selected from the group consisting of starch; microcrystalline cellulose and lactose;

sodium hydroxide and water, wherein the mole equivalents of sodium hydroxide per mole equivalents of the poorly soluble drug substance is from 0.5 to 1.5.

18. The pharmaceutical formulation of claim 17 wherein SR48692 is present in an amount of 1 to 30% by weight.

19. The pharmaceutical formulation of claim 17 further including polyethylene glycol.

20. The pharmaceutical formulation of claim 17 wherein the water is present in an amount from 0.1 to 20% by weight.

21. A pharmaceutical formulation consisting essentially of:
   a) a poorly soluble drug substance;
   b) xylitol; and
   c) Transcutol.

22. The pharmaceutical formulation of claim 21 further comprising a base.

23. A method of preparing the pharmaceutical formulation of claim 21 comprising the steps of:
   a) dissolving a poorly soluble drug substance in Transcutol; and
   b) adding the solution to xylitol.

24. A method for preparing the sodium salt of a poorly soluble organic acid drug for use in solid formulations, comprising
   (a) bringing said poorly soluble organic acid drug into intimate contact with a conversion aid to provide a drug/aid mix;
   (b) adding a concentrated aqueous solution containing at least one equivalent of sodium hydroxide to said drug/aid mix;
   (c) mixing said sodium hydroxide and drug/aid mix until said drug is greater than 95% in the form of its sodium salt;
   said conversion aid chosen from the group consisting of PEG, mannitol and polysorbate, said method allowing conversion of said poorly soluble organic acid drug into its sodium salt substantially in the solid phase.

25. A method according to claim 24 wherein said poorly soluble organic acid drug is SR48692.

26. A method according to claim 25 wherein said conversion aid is chosen from the group consisting of PEG 400, mannitol and polysorbate 20.

27. A method according to claim 26 wherein said conversion aid is from 5 to 35 parts of mannitol to 40 to 60 parts by weight of SR48692 and from 1.001 to 1.15 equivalents of sodium hydroxide is added.

28. A method according to claim 26 wherein said conversion aid is from 0.5 to 15 parts of polysorbate 20 to 35 to 55 parts by weight of SR48692 and from 1.001 to 1.1 equivalents of sodium hydroxide is added.

29. A method according to claim 26 wherein said conversion aid is from 2 to 60 parts of PEG 400 to 40 to 60 parts by weight of SR48692 and from 1.001 to 1.1 equivalents of sodium hydroxide is added.

30. A method according to any one of claims 24 to 29 further comprising the steps of
   (d) adding sufficient water to prepare a slurry;
   (e) adding excipients to form a wetted powder; and
   (f) drying to less than 15% by wt water.

31. A method according to claim 30 further comprising forming said solid into a tablet.

32. A method according to claim 30 further comprising filling said solid into a capsule.

33. A pharmaceutical formulation comprising
   (a) from about 40 parts by weight to about 60 parts by weight of the reaction product of SR48692

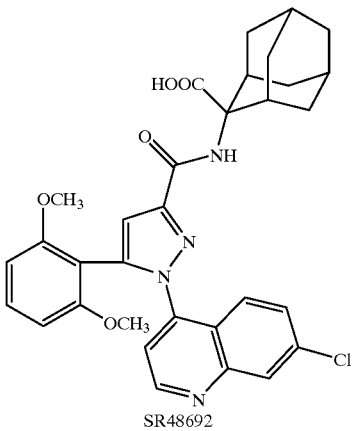

SR48692 with more than 1.0 equivalent of NaOH;
   (b) from 2 to 60 parts by weight of polyethylene glycol of molecular weight 200–800; and
   (c) less than 15 wt % water.

34. The formulation of claim 33 wherein the polyethylene glycol has a nominal molecular weight of 400.

35. A pharmaceutical formulation according to claim 33 comprising
   (a) from about 40 wt % to about 60 wt % of the reaction product of SR48692 with more than 1.0 equivalent of NaOH;
   (b) from 2 to 60 wt % polyethylene glycol of molecular weight 200–800; and
   (c) less than 15 wt % water.

36. A pharmaceutical formulation comprising
   (a) from about 40 parts by weight to about 60 parts by weight of the reaction product of SR48692

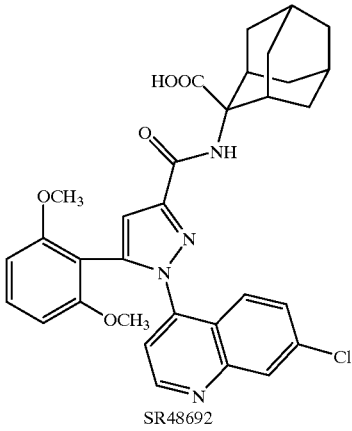

SR48692 with more than 1.0 equivalent of NaOH;
   (b) from 5 to 35 parts by weight of mannitol; and
   (c) less than 15 wt % water.

37. A pharmaceutical formulation comprising
   (a) from about 40 wt % to about 60 wt % of the reaction product of SR48692 with more than one equivalent of NaOH
   (b) from 5 to 35 wt % mannitol; and
   (c) less than 15 wt % water.

38. A pharmaceutical formulation comprising
(a) from about 35 parts by weight to about 55 parts by weight of the reaction product of SR48692

[Chemical structure of SR48692 showing HOOC-adamantyl group connected via amide to a pyrazole bearing two OCH₃-substituted phenyl and 7-chloroquinolin-4-yl groups]

with more than one equivalent of NaOH;
(b) from 0.5 to 15 parts by weight of polysorbate 20; and
(c) less than 15 wt % water.

39. A pharmaceutical formulation according to claim 38 comprising
(a) from about 35 wt % to about 55 wt % of the reaction product of SR48692 with more than one equivalent of NaOH;
(b) from 0.5 to 15 wt % polysorbate 20; and
(c) less than 15 wt % water.

40. A hard gelatin capsule filled with a pharmaceutical formulation according to any one of claims 33–39.

41. A pharmaceutical formulation according to any one of claims 33–39 in the form of a tablet.

42. A pharmaceutical formulation comprising
(a) from about 35 to about 55 parts by weight of the sodium salt of SR48692

[Chemical structure showing NaOOC-adamantyl group connected via amide to the same pyrazole-quinoline scaffold]

(b) from 0.5 to 15 parts by weight of polysorbate 20; and
(c) less than 15 wt % water.

43. A pharmaceutical formulation according to claim 42 comprising
(a) from about 35 wt % to about 55 wt % of the sodium salt of SR48692
(b) from 0.5 to 15 wt % polysorbate 20; and
(c) less than 15 wt % water.

44. A pharmaceutical formulation comprising
(a) from about 40 to about 60 parts by weight of the sodium salt of SR48692

[Chemical structure showing NaOOC-adamantyl group connected via amide to the same pyrazole-quinoline scaffold]

(b) from 2 to 60 parts by weight of polyethylene glycol of molecular weight 200–800; and
(c) less than 15 wt % water.

45. A pharmaceutical formulation according to claim 44 comprising
(a) from about 40 wt % to about 60 wt % of the sodium salt of SR48692;
(b) from 2 to 60 wt % polyethylene glycol of molecular weight 200–800; and
(c) less than 15 wt % water.

46. The formulation of claim 44 wherein the polyethylene glycol has a nominal molecular weight of 400.

47. A pharmaceutical formulation comprising
(a) from about 40 to about 60 parts by weight of the sodium salt of SR48692

[Chemical structure showing NaOOC-adamantyl group connected via amide to the same pyrazole-quinoline scaffold]

(b) from 5 to 35 parts by weight mannitol; and
(c) less than 15 wt % water.

48. A pharmaceutical formulation according to claim 47 comprising
(a) from about 40 wt % to about 60 wt % of the sodium salt of SR48692;
(b) from 5 to 35 wt % mannitol; and
(c) less than 15 wt % water.

49. A hard gelatin capsule filled with a pharmaceutical formulation according to any one of claims 42–48.

50. A pharmaceutical formulation according to any one of claims 42–48 in the form of a tablet.

* * * * *